United States Patent [19]

Polaschegg

[11] Patent Number: 4,997,570
[45] Date of Patent: Mar. 5, 1991

[54] METHOD AND DEVICE FOR ULTRAFILTRATION DURING HEMODIALYSIS

[75] Inventor: Hans-Dietrich Polaschegg, Oberursel, Fed. Rep. of Germany

[73] Assignee: Fresenius AG, Bad Homburg, Fed. Rep. of Germany

[21] Appl. No.: 431,555

[22] Filed: Nov. 3, 1989

[30] Foreign Application Priority Data

Nov. 4, 1988 [DE] Fed. Rep. of Germany ....... 3837498

[51] Int. Cl.⁵ .................. B01D 61/28; B01D 61/34
[52] U.S. Cl. ................................. 210/646; 210/739;
210/744; 210/91; 210/123; 210/314;
210/321.65; 210/321.71; 210/321.72; 210/806;
210/929
[58] Field of Search ............... 210/646, 647, 739, 744,
210/121, 123, 321.71, 321.72–321.81, 314,
321.65, 929, 806, 470, 91, 97

[56] References Cited

U.S. PATENT DOCUMENTS

| | | | |
|---|---|---|---|
| 4,267,040 | 5/1981 | Schäl | 210/104 |
| 4,477,342 | 10/1984 | Allan et al. | 210/321.71 |
| 4,530,759 | 7/1985 | Schäl | 210/929 |
| 4,618,343 | 10/1986 | Polaschegg | 210/646 |
| 4,770,769 | 9/1988 | Schael | 210/929 |
| 4,857,199 | 8/1989 | Cortial | 210/321.65 |
| 4,935,125 | 6/1990 | Era et al. | 210/321.65 |

*Primary Examiner*—W. Gary Jones
*Attorney, Agent, or Firm*—Marshall, O'Toole, Gerstein, Murray & Bicknell

[57] ABSTRACT

A method and a device for ultrafiltration during hemodialysis are described in which ultrafiltrate fluid, before removal from the dialysis circuit, is passed through a balancing device, which is also used as ultrafiltrate pump. For this purpose, a controller controls and actuates inlet, outlet, and dialyzer valves, in such a way that a desired amount of ultrafiltrate, corresponding to the filling volume of a balancing chamber or a multiple thereof, is introduced to the discharge through the balancing chamber. In order to carry out continuous ultrafiltration during hemodialysis, a predetermined amount of air is introduced to the dialysis fluid flow circuit through an air separator and is then pumped off during hemodialysis so that a corresponding amount of ultrafiltrate is obtained.

15 Claims, 4 Drawing Sheets

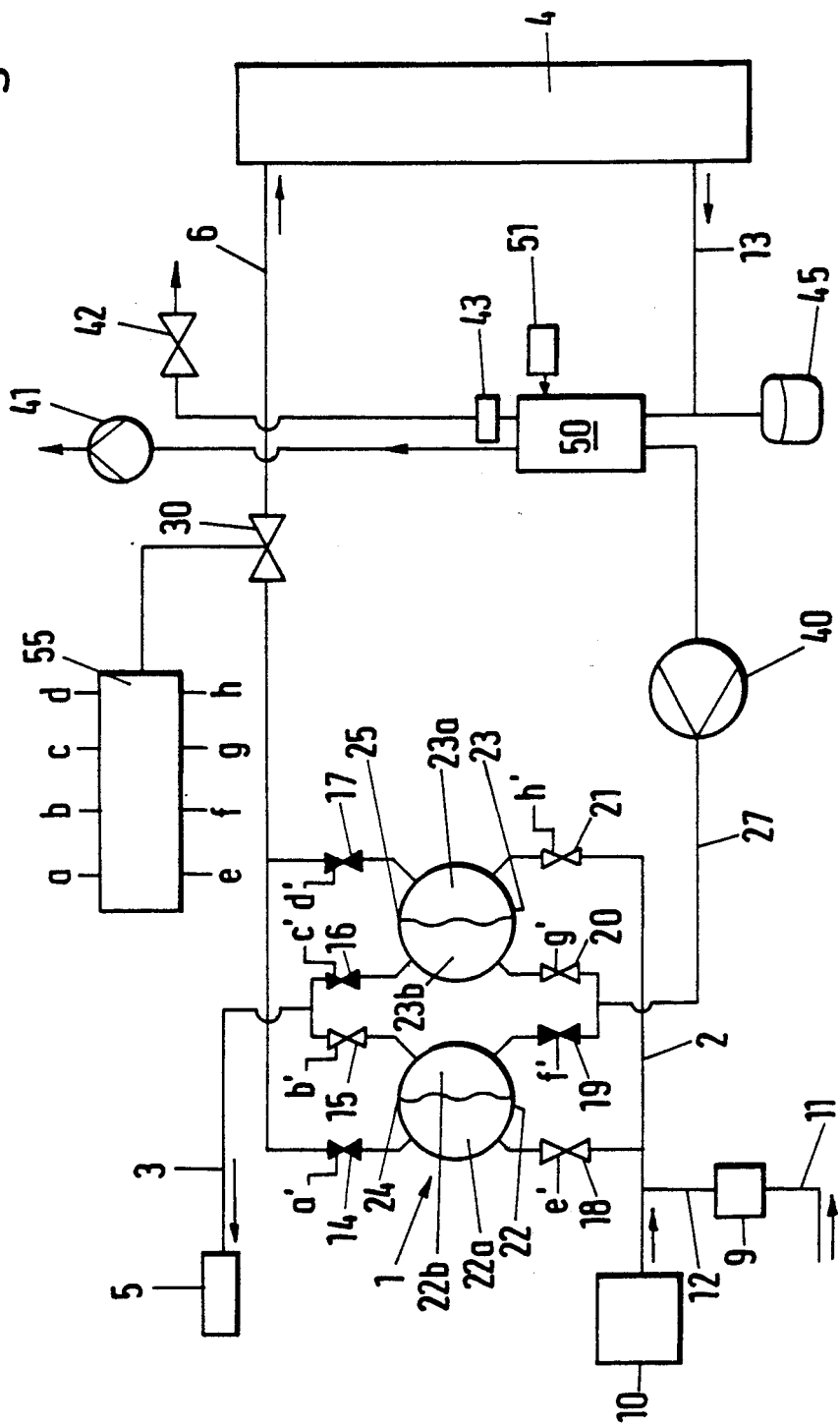

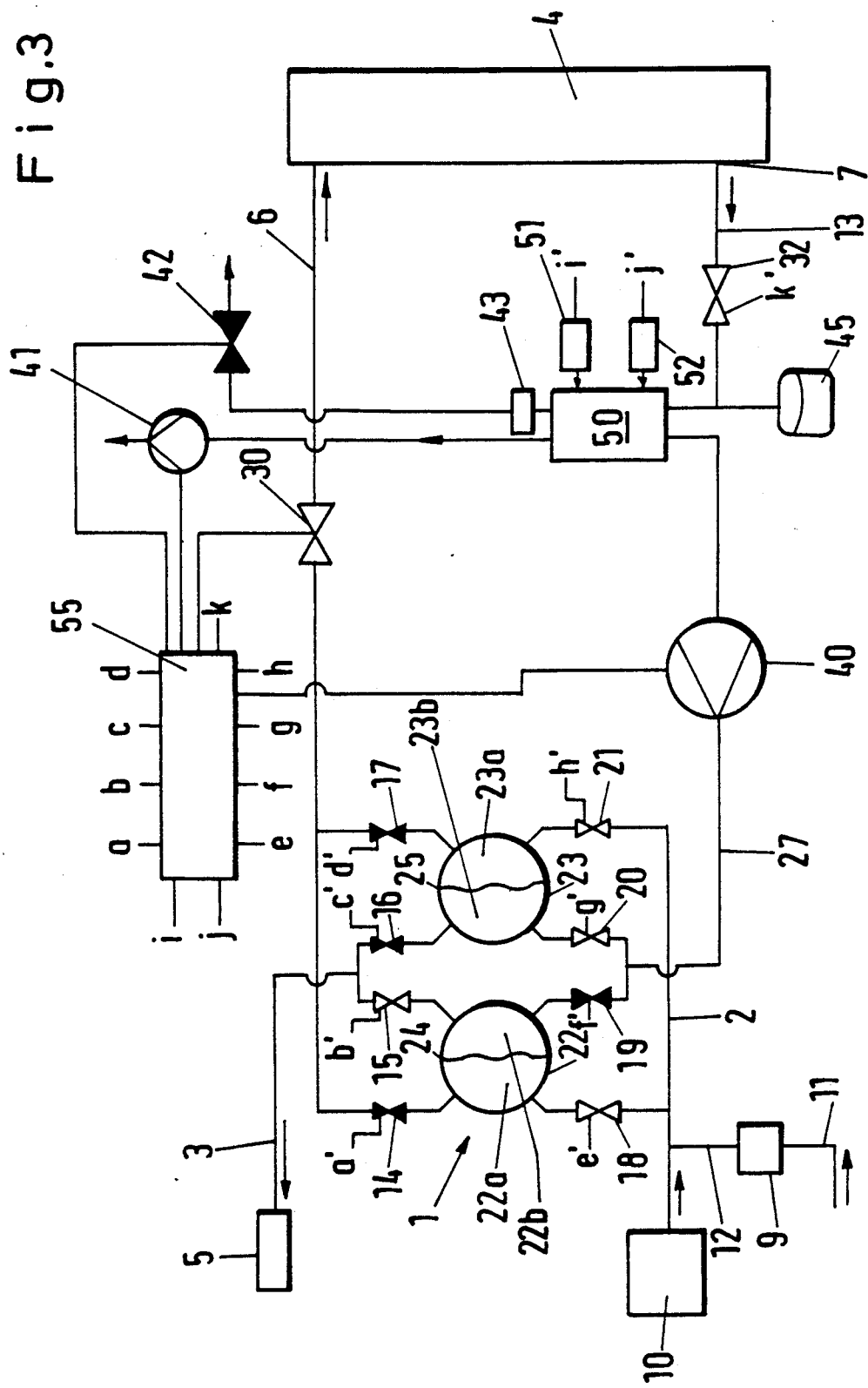

METHOD AND DEVICE FOR ULTRAFILTRATION DURING HEMODIALYSIS

BACKGROUND OF THE INVENTION

1. Field of the Invention

The invention relates generally to a method and apparatus for ultrafiltration during hemodialysis in which dialysis fluid is passed through a balancing device equipped with shut-off valves and balancing chambers connected to the dialyzer, and the ultrafiltrate is removed in an accurately predetermined amount.

2. Related Technology

West German Patent 28 38 414 (Oct. 31, 1984) and its counterpart U.S. Pat. Nos. 4,267,040 (May 12, 1981); 4,530,759 (July 23, 1985); and 4,770,769 (Sept. 13, 1988), the respective disclosures of which are hereby incorporated herein by reference, disclose a device which has a balancing device including two chambers separated by a movable element, each chamber having an inlet conduit for the introduction of fresh dialysis fluid and an outlet conduit for discharge of used dialysis fluid. Shut-off valves are disposed in the inlet and outlet conduits and are connected and switched (activated) by a control unit. A pump is disposed in the dialysis fluid flow circuit between the dialyzer and the balancing device to move the used dialysis fluid. A dialysis valve is provided in the dialyzer inlet conduit and an air separator is provided in the discharge conduit of the dialyzer.

This apparatus is operated in such a way that fresh dialysis fluid from a dialysis fluid source is introduced alternately to the two balancing chambers through appropriate switching of the shut-off valves in the inlet conduits. At the same time, fresh dialysis fluid is introduced from an already filled space in the other balancing chamber, as a result of which the toxins that are desired to be removed from the blood are removed by diffusion as the blood flows through the dialyzer. The dialysis fluid that becomes used dialysis fluid as a result of this diffusion is then pumped into a second space of the same balancing chamber from which the used dialysis fluid can be discharged.

A portion of the fluid circuit which is included between the balancing device and the dialyzer behaves as a closed system with a constant volume. In order to remove liquid from this system, a removal device is connected to a discharge.

The amount of fluid that is removed from the system with the aid of the removal device must be replaced by an equal amount of fluid based on the properties of the balancing device mentioned above, which amount of fluid goes from the blood side to the dialysis fluid side of the dialyzer membrane. Thus, the amount of fluid removed with the aid of the removal device corresponds to the amount of fluid that goes through the membrane of the dialyzer (i.e., the ultrafiltrate). The removal device, which behaves as an ultrafiltrate pump, is designed in such a way that control of the ultrafiltration is possible.

The balancing device and the removal device must be highly accurate and precise. In hemodialysis treatment, typically, about 200 liters of dialysis solution are passed through the dialyzer. The amount of ultrafiltrate is typically about 2 to 3 liters and must be able to be determined accurately with a deviation of the order of only 0.1 to 0.2 liter. Accordingly, the error which occurs in the balancing apparatus should not exceed an order of magnitude of 1 per thousand, if possible. In order to be able to remove an accurately predetermined amount of ultrafiltrate from the dialysis fluid circuit with the required accuracy, the removal device is equipped with a volumetric membrane pump, where each individual stroke of the pump corresponds to a unit amount of ultrafiltrate. The removal is done through a conduit from the lower part of an air separator disposed in the dialysis circuit, in order to ensure that only bubble-free fluid is removed. The outlet of the ultrafiltration pump or of the removal device is connected to the discharge conduit through a shut-off valve.

Although this prior art device operates accurately and reliably, it is desirable to simplify equipment of this type, especially to reduce the number of moving components and to minimize the need for calibration and safety-technological controls which must be carried out from time to time. These calibration processes and controls also concern the ultrafiltrate removal device.

SUMMARY OF THE INVENTION

Therefore, an object of the invention is to provide a method by which a predeterminable degree of ultrafiltration can be carried out in a simple fashion without an additional ultrafiltrate pump. It is also an object of the invention to provide a device for carrying out this method.

The invention provides a method of filtering or dialyzing blood, called hemodialysis or hemodiafiltration, wherein a dialysis fluid is passed through a dialyzer fluid circuit which includes a balancing device equipped with a series of shut-off valves and balancing chambers. The balancing apparatus is connected to the dialyzer, so that the ultrafiltrate fluid product is removed from the dialyzer fluid circuit in an accurately predetermined amount. The inventive method includes the steps of interrupting the dialysis fluid path between consecutive hemodialysis cycles and switching the shut-off valves of the balancing device in such a way that the fresh dialysis fluid located in one of the balancing chambers is transferred to the other balancing chamber during flow of at least the ultrafiltrate product fluid into one of the balancing chambers.

The ultrafiltrate fluid is preferably removed from the dialysis fluid path in such an amount as to correspond to the filling volume of the balancing device, or a multiple thereof. Also, preferably the dialysis fluid path is interrupted between the balancing device and the dialyzer for the duration of the removal of the ultrafiltrate product into the balancing device. Preferably, the ultrafiltrate product is removed continuously and together with or at the same time as the used dialysis fluid is removed from the dialysis fluid circuit through the balancing device, so that during the interruption of the dialysis fluid path between the balancing device and the dialyzer air is introduced into the dialysis fluid path in an amount which corresponds to the filling volume of one balancing apparatus chamber, or a multiple thereof, and so that during hemodialysis the same volume of air is removed continuously from the dialysis fluid path, so that a volume of ultrafiltrate product is obtained in the dialysis fluid path which corresponds to the volume of air which was introduced into the system. The desired volume of air is preferably introduced through an air separator, and is preferably introduced at such a rate that the pressure does not increase in the dialysis fluid path. The dialysis fluid path can also be interrupted between the dialyzer and the air separator and the desired amount of air can be removed or aspirated with the aid of the dialyses fluid pump through the air separator.

This invention also provides a device for purifying blood by hemodiafiltration using a dialysis fluid and air, including as components thereof a dialyzer and a fluid balancing system which comprises a dialysis unit including as components thereof:

(a) a balancing device containing two dialyzer fluid-fillable chambers which are separated by a movable element, with at least one means for recognizing at least one final position of the movable element in its respective ultrafiltration and hemodialysis modes, each of the chambers having an inlet conduit for introducing fresh dialysis fluid and an outlet or discharge conduit for removing the used dialysis fluid, the outlet conduit being connected to a fluid discharge port;

(b) shut-off valves disposed in the inlet and discharge conduits of the balancing device;

(c) a dialyzer valve connected between the fresh dialyzer fluid side of the balancing device and the dialyzer;

(d) a dialyzer having inlet and discharge ports connected in the apparatus circuit, disposed between the dialyzer valve and an air separator;

(e) an air separator connected between the dialyzer fluid discharge port and a dialyzer fluid pump;

(f) a dialysis fluid pump disposed in the dialysis fluid circuit between the air separator and the balancing apparatus for transporting the used dialysis fluid or ultrafiltrate fluid to the balancing device;

(g) a preparation unit to provide fresh dialysis fluid to the dialysis fluid circuit through the balancing device; and, (h) a control unit connected to the shut-off valves of the balancing device and the dialyzer valve.

The components (a) to (h) are connected in the circuit so that the control unit (h) controls and switches (opens/closes) the shut-off valves of the balancing device and the dialyzer valve in such a way as to permit the ultrafiltrate product to be discharged in a predetermined amount through a chamber of the balancing device to the discharge port. Preferably, the control unit controls the shut-off valves and dialysis valve in such a way that the amount of ultrafiltrate fluid removed substantially corresponds to the volume needed to fill one of the filling chambers of the balancing device. The control unit can also be designed for the control and switching of the shut-off and dialysis valves so that during the inflow of the ultrafiltrate fluid product or the used dialysis fluid into one of the balancing chambers the fresh dialysis fluid located in the other section of the balancing chamber can be transferred into the other balancing chambers. The device of the invention can also be designed so that the pump arrangement associated with the air separator can introduce air to or remove air from the air separator, e.g., by the use of a bidirectional operating air pump connected to the air separator. The air separator can have sensors arranged thereon so as to limit and control the volume of one of the balancing chambers or to a multiple of such volume. The device of the invention can also include a valve on the discharge line side of the dialyzer between the dialyzer discharge outlet and the inlet of the air separator.

THE DRAWINGS

FIG. 1 a,b are simplified schematic illustrations of the principle of a dialysis fluid flow circuit with a balancing device according to a first embodiment, showing alternate ultrafiltration (FIG. 1a) and hemodialysis modes (FIG. 1b).

FIG. 3 is a simplified schematic illustration of the principle of the dialysis fluid flow circuit of the invention according to another embodiment, showing air introduction to the separator via use of the dialyzer fluid pump and a shut-off valve at the outlet end of the dialyzer.

DETAILED DESCRIPTION OF THE INVENTION

Figure 1B:
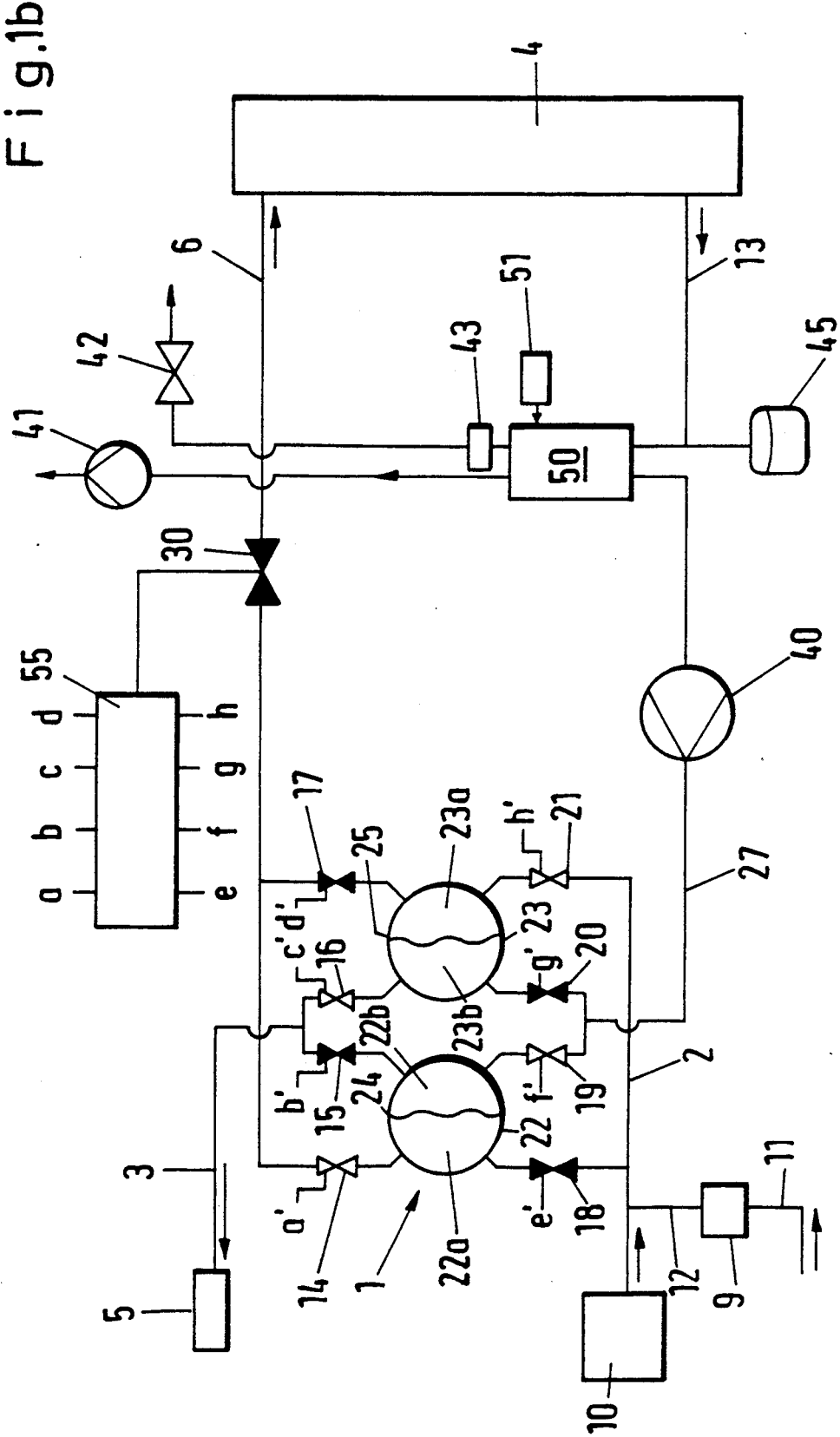

Until now, the ultrafiltrate was removed through a separate removal device in the dialysis fluid circuit between the dialyzer outlet and the balancing device. According to the invention, the ultrafiltrate goes through the balancing device before removal from the dialysis circuit. In this way, the entire removal device for the ultrafiltrate can be omitted. From the balancing device, the ultrafiltrate and the used dialysis fluid are introduced to the discharge. In addition to eliminating the ultrafiltrate pump, this method furthermore provides the advantage that the filling volume of the balancing chamber can be used for the determination of the amount of ultrafiltrate. Since the filling volume of a balancing chamber is typically 30 mL, by periodic filling of the balancing chamber several times with ultrafiltrate, the desired amount of ultrafiltrate, which is about 2 to 3 L, can be determined in a precise, accurate manner and can be removed from the dialysis fluid path.

According to a first embodiment, in order to carry out ultrafiltration the shut-off valves in the inlet and outlet conduits of the balancing chambers are first switched in such a way that one of the balancing chambers is filled completely with fresh dialysis fluid and the other balancing chamber is filled completely with used dialysis fluid. Then the dialysis fluid path between the balancing device and the dialyzer is interrupted. Expediently, this is done with the aid of a dialyzer valve. After this dialyzer valve is closed, used dialysis fluid is pumped from the dialyzer, with the aid of the dialysis fluid pump, whereby, after a relatively short time, due to the interruption of the inflow of fresh dialysis fluid, the pressure will be reduced in the dialysis chamber. As a result of this, a fluid called "ultrafiltrate" is removed from the blood and pumped by the dialysis fluid pump into a first space in the balancing chamber, a second space of which is filled with fresh dialysis fluid. Since, as a result of the interruption of the dialysis fluid path, the displaced fresh dialysis fluid cannot be introduced to the dialyzer, with the aid of suitable switching of the inlet and discharge valves of the balancing chambers, the fresh dialysis fluid is diverted into the empty space of the other balancing chamber, as a result of which, at the same time, the used dialysis fluid located in this chamber is pushed toward the discharge. After the first balancing chamber is filled completely with ultrafiltrate, the first pass of ultrafiltration is completed and the inlet and outlet valves of the balancing chambers are switched to hemodialysis operation. By interruption of the hemodialysis, in this way, an ultrafiltration cycle can be effected.

This method, which causes uneven removal of ultrafiltrate, can be improved by a further embodiment of the invention in such a way that the ultrafiltrate is removed continuously. For this purpose, before carrying out the ultrafiltration and hemodialysis, an amount of air corresponding to the filling volume of the balancing device or a multiple thereof is introduced into the dialysis fluid circuit. The desired amount of air is introduced in the usual way between the dialyzer and the balancing device into the air separator located in the dialysis fluid circuit. As a result, the dialysis fluid circuit is again interrupted until the desired amount of air is found in the air separator.

Inlet of air can be carried out in two different ways. According to a preferred embodiment, an air pump is connected to the air separator, which, after interruption of the dialysis fluid path between the balancing apparatus and the dialyzer, pumps the desired amount of air into the air separator by closing the dialysis valve. As a result, the dialysis fluid pump also remains in operation. By suitable adjustment of the transport rates of the two pumps, a pressure increase in the dialysis fluid path is avoided. The air separator has two sensors which are spaced from each other or it has an analog level meter arranged in such a way that the two sensors or the minimum and maximum position of the level sensor encompass approximately the filling volume of a balancing chamber. Thus, during this process, no fluid is removed from the blood, but the closed system is partially filled with air in a controlled manner. This process requires only a few seconds of time. Then the valves are again switched to the dialysis mode and the air pump now begins to operate in the reverse direction, by removing the air which was pumped before into the dialysis fluid path from the air separator, as a result of which ultrafiltration of liquid from the blood is achieved. For the case where the air separator must collect additional air during hemodialysis, the air pump remains in operation until the upper sensor detects fluid.

According to another embodiment, it is possible, instead of using an air pump, to pump the air into the dialysis fluid path with the aid of the dialysis fluid pump, which is disposed between the air pump and the balancing device. For this purpose, the dialysis fluid path is interrupted between the outlet of the dialyzer and the air separator with the aid of another valve, in order to prevent aspiration of used dialysis fluid. When, in this case, the dialysis fluid pump is allowed to continue to operate, air is pumped through the air pump into the air separator. In order to accelerate aspiration, the pump power of the dialysis fluid pump can be increased for a short period. For this purpose, the dialysis fluid pump is switched appropriately by the control unit. The determination of the amount of air is then done with the aid of the two sensors arranged in the air separator or through an analog level meter. Then the dialysis fluid path is opened again and the valves are switched to dialysis operation. In this case, too, subsequently, during dialysis, with the aid of the air pump connected to the air separator, the amount of air aspirated previously is again removed from the dialysis liquid circuit. As a result of this, the liquid level in the air separator increases again and, after both sensors detect fluid, the ultrafiltration is completed, whereupon an amount of ultrafiltrate corresponding to the air volume is obtained. Then the dialysis fluid path is filled with air again and the process begins anew. In this way, it is possible to remove ultrafiltrate continuously during dialysis.

Removal of the desired amount of ultrafiltrate can be distributed to an arbitrary number of filling cycles of the balancing chambers by appropriate control of the air pump. By suitable selection of the chamber volume of the air separator, this can be a multiple of the filling volume of a balancing chamber, so that, in the extreme case, when the volume of the air separator corresponds to two to three liters, it has to be filled with air only once.

Upon continuous removal of the ultrafiltrate during dialysis, the amount of fluid which leaves the dialyzer is increased by the amount of ultrafiltrate in comparison to the amount that is introduced as fresh dialyzing fluid to the dialyzer. Since this additional amount is collected by removal of the air from the air separator, the mode of operation of the balancing chamber does not change at all in comparison to the dialysis method of the art. When aspirating the air into the air separator, the used dialysis fluid in the air separator is pumped into the empty space of the balancing chamber, which is filled with fresh dialyzing fluid, whereby, at the same time, this fresh dialyzing fluid is pushed into the other balancing chamber, where again the used dialysis fluid found there is displaced into the discharge. This is achieved by appropriate control of the inlet and discharge valves.

The inventive device has no removal device and thus no separate ultrafiltrate pump. The discharge of the dialyzer is connected directly to the air separator, which is connected to the balancing apparatus through the dialysis fluid pump. According to the invention, the device for controlling the inlet and discharge valves of the balancing installation, as well as the dialyzer valve and possibly the additional shut-off valves between the dialyzer outlet and air separator, is designed in such a way that the ultrafiltrate can be transferred in a predetermined amount through a chamber of the balancing device to the discharge. The shut-off valves are thus controlled in such a way that the amount of ultrafiltrate discharged always corresponds to a filling volume of a balancing chamber or to a multiple of it.

According to a first embodiment, the control device is designed in such a way that it closes the dialyzer valve between two hemodialysis cycles and controls the shut-off valves of the balancing device in such a way that the ultrafiltrate can be moved into one of the two spaces of one of the two balancing chambers with the aid of the dialysis fluid pump, while the fresh dialysis fluid, which is in the other space of the balancing chamber, is transferred into the other balancing chamber. This means that the valves between the ultrafiltration mode and hemodialysis mode are switched back and forth alternately. In the hemodialysis mode, the valves in the inlet conduits, for example, of the two right spaces of the balancing chambers, and the valves of the discharge conduits of the two left spaces of the balancing chambers are closed, while the valves in the inlet and discharge conduits of the other spaces are closed.

When going to the ultrafiltration mode, all valves of one of the two chambers are switched, while in the other balancing chamber only the valves of the left space are switched and those of the right space are maintained in the same position.

According to another embodiment, the control unit is also designed to control the air pump and/or the dialysis fluid pump. The switching position of the valves in the hemodialysis mode corresponds to that in the mode of operation described above. After one hemodialysis cycle, in which, at the same time, the ultrafiltrate is removed, the valves in the abovedescribed ultrafiltration mode are switched, and serve to pump air into the dialysis fluid path. For this purpose, the control unit controls not only the shut-off valves, but also the air pump and the dialysis fluid pump and, if desired, another shut-off valve in the dialysis fluid path between the dialyzer and air separator.

In order to carry out continuous ultrafiltration, the air separator is adapted so that air can be introduced thereinto and removed therefrom. According to a further embodiment, the air separator is equipped with a bidirectionally operating air pump, which pumps the appropriate amount of air into the air separator before ultrafiltration and then pumps out this amount of air from the air separator during ultrafiltration. In order that the particular air volume can be determined exactly, two sensors are disposed in the air separator at a distance apart from each other in such a way that they delimit the filling volume of a balancing chamber or a multiple thereof. It is also possible to use an analog level meter instead of the two sensors, the distance of which between a maximum and minimum position corresponds to a filling volume or a multiple of the filling volume of a balancing chamber.

According to another embodiment, besides the dialyzer valve between the dialyzer outlet and the air separator inlet, another valve is disposed in the dialysis fluid circuit.

Examples of the embodiments of the invention will be explained in more detail with the aid of the drawings.

In FIG. 1a, the dialysis fluid circuit is shown schematically, and includes the balancing apparatus 1 which includes two coupled chambers 22 and 23, each of which is subdivided by a movable element in the form of a membrane 24 or 25 into two spaces, 22a and 22b or 23a and 23b. These balancing chambers are supplied with fresh dialysis fluid via a conduit 2 from a dialysis fluid source 10, which is equipped with a pump as well as a metering device 9 which is supplied through a conduit 11 and in turn supplies the conduit 2 through a connection 12. In the example shown here, spaces 22a and 23a are connected to the inlet conduit 2, wherein, for the purpose of locking, shut-off valves 18 and 21 are disposed. The spaces 22a, 23a are connected with a dialysis inlet branch 6 on their outlet sides, through further shut-off valves 14 and 17, respectively; the branch 6 leads to a dialyzer 4. A dialyzer valve 30 is included in the inlet branch 6. The outlet of the dialyzer 4 is connected again with balancing apparatus 1 through a dialyzer discharge branch 13, an air separator 50 and a dialysis fluid pressure measuring device 45 as well as through a dialysis fluid pump 40 connected to air separator 50. An aeration valve 42 is connected to the air separator 50 through a sensor 43. A dialysis fluid discharge branch 27 between the dialysis fluid pump 40 and the balancing apparatus 1 is divided into two paths, which lead to spaces 22b and 23b of balancing chambers 22 and 23. Shut-off valves 19 and 20 are arranged in these two paths before the balancing chambers. Spaces 22b and 23b are connected to a discharge conduit 3 through shut-off valves 15 and 16, with the discharge conduit 3 leading to a discharge 5.

Valves 14–21 and 30 are controlled by a controller 55 having outputs a through h which are connected with valves 14–21 through electrical conductors a' to h', respectively.

In FIG. 1a, valves 14, 16, 17 and 19 are dark (i.e., open) and valves 15, 18, 20 and 21 and the dialyzer valve 30 are light (i.e., closed). This switching situation (called "ultrafiltration mode") corresponds to the first embodiment of the inventive method in which the space 22a is filled completely with fresh dialysis fluid and the space 23b is filled completely with used dialysis fluid. When when the dialysis fluid pump 40 is in operation with the dialysis valve 30 closed, a reduction in pressure is produced in the dialyzer 4, as a result of which ultrafiltrate is removed from the blood circulation path (not shown). This ultrafiltrate is introduced through the line 27 and the open valve 19 of the balancing chamber 22 and then into the space 22b, whereby, at the same time, fresh dialysis fluid is introduced into the line 6 from the space 22a through open valve 14 and open valve 17 into space 23a of the balancing chamber 23. The used dialysis fluid from the chamber 23b is then introduced via the discharge line 3 to the discharge 5 through the open valve. 16. After space 22b of balancing chamber 22 is filled completely with ultrafiltrate, valves 14–21 and 30 are controlled by the controller 55 in such a way that valves 14, 16, 19 and 21 will close and valves 15, 17, 18, 20 and 30 will open. (This is the hemodialysis mode.) This switching position is shown in FIG. 1b. In this position of the valves, the hemodialysis can be performed as is known from West German Patent 28 38 414. In the next dialysis cycle, space 23b is filled with used dialysis fluid and space 22a is filled with fresh dialysis fluid.

In the case where air is separated in the dialysis fluid path in the air separator 50, the liquid level in the air separator drops so that an air/liquid sensor 51 detects air in air separator 50. In this case, a pump 41 is activated to pump off the excess air until the pump is deactivated by a signal of the sensor 51.

Figure 2:
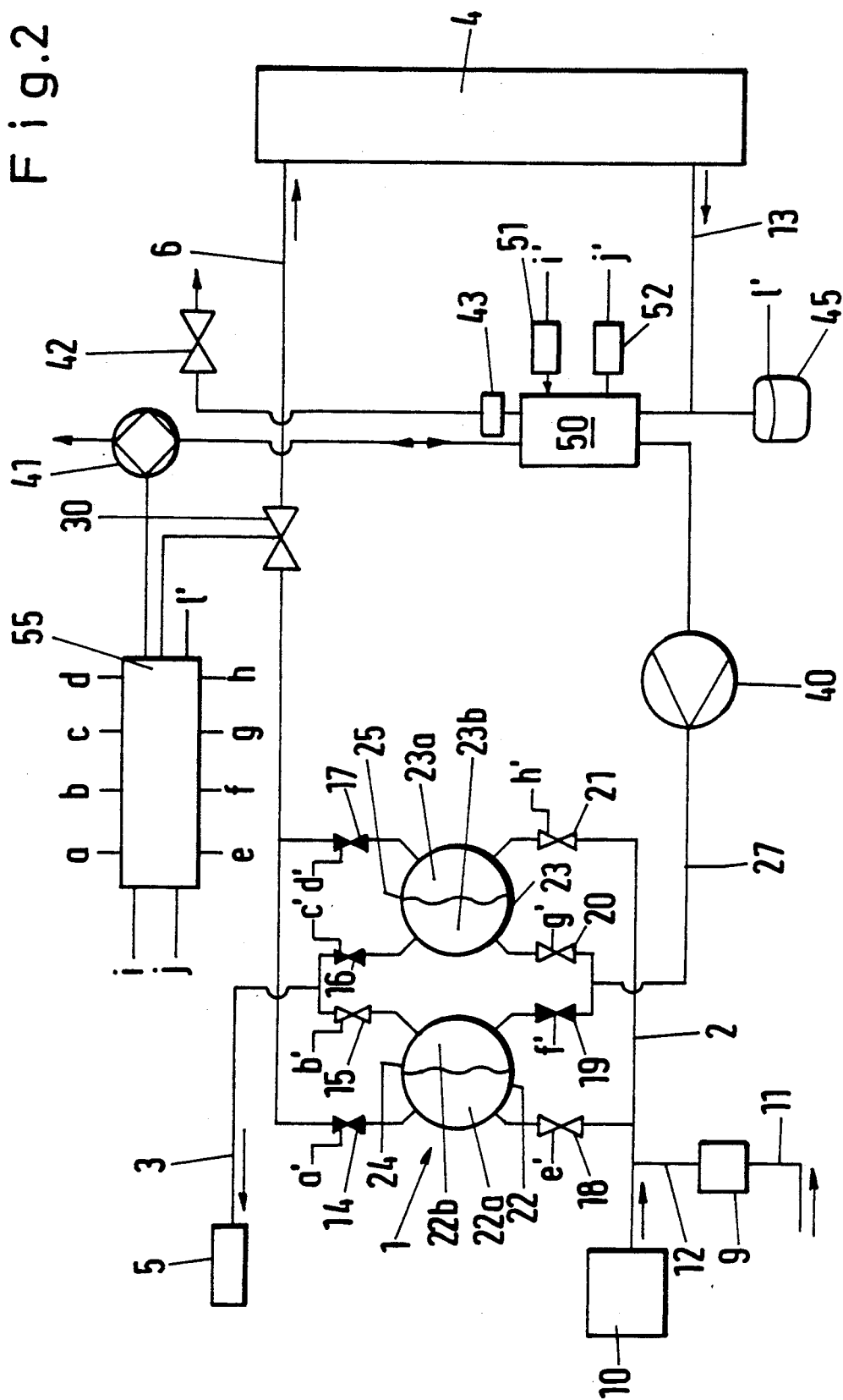
FIG. 2 is a simplified schematic illustration of the principle of the dialysis fluid flow circuit according to another embodiment, showing bidirectional air movement.

FIG. 2 shows a further embodiment wherein the air separator 50 is equipped with an upper sensor 51 and a lower sensor 52 which are connected to inputs i and j of the controller 55 through electrical conductors i' and j'. Instead of the analog level sensor or the two sensors 51, 52, a single sensor 51 can be used in combination with a volumetric pump. Since the pressure in the system is known through the dialysis fluid pressure sensor 45, the pump 41 can be controlled by control unit 55 in such a way that, taking into consideration the general gas law, a previously determinable amount of dialysis fluid is displaced from air separator 50. For this purpose, the dialysis fluid pressure sensor 45 is connected with input 1 of control unit 55 through electrical conductor 1'.

Valves 14, 16, 17, 19 or 15, 18, 20, 21, respectively, are shown dark and light, respectively, which indicates that these valves are switched open or closed, respectively, by controller 55. The switching position of valves 14 to 21 corresponds in this case to the position shown in FIG. 1a.

Before beginning the ultrafiltration, according to the embodiment of FIG. 2 air is first pumped into air separator 50 through air pump 41, which operates as a bidirectional pump, and is also connected to controller 55, whereby the pumping rate is controlled in such a way that the pressure at the dialysis fluid pressure sensor 45 does not increase. Pump 41 pumps air until air is detected at the lower sensor 52. Sensors 51 and 52 are positioned in such a way that the volume between them corresponds approximately to the balancing chamber volume.

The dialysis fluid displaced in this way is pumped through the valve 19 into space 22b of the balancing chamber 22 with the aid of the pump 40, the pumping rate of which is adjusted to that of air pump 41. At a predetermined rate, either of pump 40 or of pump 41, the other pump can be controlled in such a way that the dialysis fluid pressure measured with the aid of the dialysis fluid pressure sensor 45 remains constant.

At the same time, the fresh dialysis fluid located in space 22a of balancing chamber 22 is pumped through valve 14 and also through open valve 17 into space 23a of the second balancing chamber 23.

After the desired amount of air has been pumped into air separator 50, the dialysis valve 30 and valves 14 to 21 are opened by the controller 55 in the dialysis mode, as shown in FIG. 1b, and air pump 41 is switched to the deaeration operation. In this case, the air pump 41 again pumps the air from the air separator 50 over a desired period of time, until the upper sensor 51 again detects liquid, at which point and air pump 41 is deactivated. In this way, continuous ultrafiltration during hemodialysis is possible.

FIG. 3 shows another embodiment. In this example, an additional valve 32 is disposed in the dialyzer discharge path 13 which connects the discharge 7 of the dialyzer with the air separator 50. The valve 32 is connected with input k of the controller 55 through a conductor k'. Before beginning ultrafiltration, in order to prevent aspiration of the used dialysis fluid, the valve 32 is closed by the controller 55, while the dialysis fluid pump 40 continues to run. At the same time, the air pump 41 is shut off and the aeration valve 42 of air separator 50, which is also connected to controller 55, is opened. Correspondingly, the valve 42 is shown dark and remains open until the lower sensor 52 detects air. The switching position of valves 14 to 21 is the same as shown in FIG. 2. In order to aspirate the air as quickly as possible, the pumping rate of the dialysis fluid pump 40 can be increased for a short time by controlling the control unit 55.

When the desired amount of air is in air separator 50, the valve 42 is closed and valves 30 and 32 are opened. At the same time, valves 14 to 21 are switched to the dialysis mode (see FIG. 1b). At the same time, in this mode of operation, pump 41, which operates on one side, is put into operation by controller 55, and then during a predetermined time period, it pumps off the amount of air 50 located in the air separator, causing fluid from the dialyzer 4 to be drawn into the separator 50. This happens until the upper sensor 51 detects fluid again. During this period, ultrafiltrate is taken from the blood circulation dialyzer as a result of the existing reduced pressure. This arrangement can be controlled especially precisely when, instead of sensors 51 and 52, an analog filling-level sensor is used. The switching of the valves during hemodialysis and ultrafiltration modes then corresponds to the switching position already described in connection with FIG. 1a.

The foregoing detailed description is given for clearness of understaing only, and no unnecessary limitations should be understood therefrom, as modifications within the scope of the invention will be apparent to those skilled in the art.

I claim:

1. A method useful in the hemodialysis of blood wherein a dialysis fluid is passed through a dialysis circuit including a dialyzer and ultrafiltrate is removed in an accurately predetermined amount, said method comprising the steps of:

(a) providing a balancing device in the dialysis circuit, the balancing device comprising shut-off valves and balancing chambers; and
    (b) removing the ultrafiltrate from the dialysis circuit through a balancing chamber of the balancing device in a controlled manner wherein the dialysis circuit is interrupted between two hemodialysis cycles and the shut-off valves of the balancing device are switched in such a way that at least the ultrafiltrate flows into one of the balancing chambers as fresh dialysis fluid contained therein is transferred into another of the balancing chambers.

2. The method of claim 1 wherein the ultrafiltrate is removed from the dialysis circuit in an amount corresponding to a filling volume of a balancing chamber or a multiple thereof.

3. The method of claim 1 wherein the dialysis circuit is interrupted between the balancing device and the dialyzer for the duration of the removal of the ultrafiltrate while the predetermined amount of ultrafiltrate flows from the dialyzer into one of the balancing chambers.

4. A method useful in the hemodialysis of blood wherein a dialysis fluid is passed through a dialysis circuit including a dialyzer and an ultrafiltrate is removed in an accurately predetermined amount alternately with removal of used dialysis fluid, said method comprising the steps of:

(a) providing a balancing device in the dialysis circuit, the balancing device comprising shut-off valves and balancing chambers;
    (b) interrupting the dialysis circuit between the balancing device and the dialyzer while introducing a volume of air corresponding to a filling volume of one of the balancing chambers, or a multiple thereof, into the dialysis circuit;
    (c) continuously removing said volume of air from the dialysis circuit during hemodialysis so that a corresponding amount of ultrafiltrate is obtained in the dialysis circuit;
    (d) continuously removing the ultrafiltrate from the dialysis circuit through the balancing device in a controlled manner wherein the shut-off valves of the balancing device are switched in such a way that at least the ultrafiltrate flows into one of the balancing chambers as fresh dialysis fluid contained therein is transferred into another of the balancing chambers and used dialysis fluid is removed through the balancing device.

5. The method of claim 4 wherein the air introduced into the dialysis circuit during said interruption is introduced at a rate such that the pressure in said circuit does not substantially increase.

6. The method of claim 4 wherein the air introduced into the dialysis circuit during said interruption is introduced through an air separator.

7. The method of claim 4 wherein the dialysis circuit is interrupted between the dialyzer and an air separator and the volume of air introduced into the dialysis circuit during said interruption is aspirated by a dialysis fluid pump through said air separator.

8. A dialysis circuit device useful for the controlled processing of a dialysis fluid, said device comprising:
    a dialyzer;
    a balancing device comprising two chambers each of which is subdivided by a movable element, each chamber having an inlet conduit for fresh dialysis fluid and an outlet conduit connected to a fluid discharge port for removing used dialysis fluid;

shut-off valves arranged in the inlet and outlet conduits;

a pump arranged for transporting used dialysis fluid;

an air separator;

a preparation unit for providing fresh dialysis fluid; and a control unit connected to the shut-off valves comprising means for controlling and switching the shut-off valves so that ultrafiltrate is discharged in a previously determined amount through a chamber of the balancing device to the fluid discharge port said control unit further comprising means for controlling transfer of fresh dialysis fluid from one balancing device chamber to the other balancing device chamber.

9. The device of claim 8 wherein the control unit and shut-off valves comprise means for controlling and switching the shut-off valves such that the discharged amount of ultrafiltrate corresponds to a filling volume of one of the chambers.

10. The device of claim 8 wherein the device further comprises means for detecting a final position of the movable element and the control unit and shut-off valves comprise means for transferring fresh dialysis fluid from one chamber to another chamber during an inflow of at least the ultrafiltrate into the chamber from which said fresh dialysis fluid is transferred.

11. The device of claim 8 further comprising means for introducing air into the air separator and means for removing air from the air separator.

12. The device of claim 8 wherein a bidirectional pump is connected to the air separator.

13. The device of claim 8 further comprising means for limiting the volume of air in the air separator to a volume corresponding to a filling volume of one of the chambers, or a multiple thereof, said limiting means comprising a lower sensor and an upper sensor disposed at said air separator.

14. The device of claim 8 further comprising an analog level meter disposed at the air separator and having a minimum position and a maximum position defining a volume corresponding to a filling volume of one of the chambers, or a multiple thereof.

15. The device of claim 8 further comprising a dialyzer valve and a valve disposed in a dialyzer discharge branch between an outlet of the dialyzer and an inlet of the air separator.

* * * * *